(12) United States Patent
Johnston et al.

(10) Patent No.: US 6,815,671 B2
(45) Date of Patent: Nov. 9, 2004

(54) SYSTEM AND METHOD FOR CHEMICAL ANALYSIS USING LASER ABLATION

(75) Inventors: Murray V. Johnston, Newark, DE (US); Derek A. Lake, Newark, DE (US); Gary A. Eiceman, Las Cruces, NM (US)

(73) Assignee: The University of Delaware, Newark, DE (US)

( * ) Notice: Subject to any disclaimer, the term of this patent is extended or adjusted under 35 U.S.C. 154(b) by 0 days.

(21) Appl. No.: 10/297,648

(22) PCT Filed: Jun. 7, 2001

(86) PCT No.: PCT/US01/18468

§ 371 (c)(1), (2), (4) Date: Jul. 3, 2003

(87) PCT Pub. No.: WO01/95999

PCT Pub. Date: Dec. 20, 2001

(65) Prior Publication Data

US 2004/0011952 A1 Jan. 22, 2004

Related U.S. Application Data

(60) Provisional application No. 60/210,610, filed on Jun. 9, 2000.

(51) Int. Cl.[7] .............................................. B01D 59/44
(52) U.S. Cl. ....................................................... 250/287
(58) Field of Search ................................ 250/288, 286, 250/287, 282, 281

(56) References Cited

U.S. PATENT DOCUMENTS

| | | | |
|---|---|---|---|
| 4,445,038 A | * | 4/1984 | Spangler et al. ............ 250/382 |
| 5,189,301 A | | 2/1993 | Thekkadath |
| 5,227,628 A | * | 7/1993 | Turner ......................... 250/286 |
| 5,455,417 A | | 10/1995 | Sacristan |
| 5,543,331 A | * | 8/1996 | Puumalainen ................ 436/153 |
| 5,905,258 A | | 5/1999 | Clemmer et al. |
| 5,968,837 A | | 10/1999 | Doring et al. |
| 5,998,215 A | * | 12/1999 | Prather et al. ............... 436/173 |
| 6,033,546 A | | 3/2000 | Ramsey |
| 6,118,120 A | | 9/2000 | Fenn et al. |
| 6,124,592 A | | 9/2000 | Spangler |
| 6,509,562 B1 | * | 1/2003 | Yang et al. .................. 250/287 |
| 6,653,627 B2 | * | 11/2003 | Guevremont et al. ........ 250/288 |

OTHER PUBLICATIONS

Gary A. Eiceman et al., *Ion Mobility Spectrometry* (1994).

* cited by examiner

*Primary Examiner*—Jack Berman
*Assistant Examiner*—Johnnie L. Smith, II
(74) *Attorney, Agent, or Firm*—Connolly Bove Lodge & Hutz LLP

(57) ABSTRACT

A system and method for chemically analyzing single particles in a high velocity gas flow. The system comprises an ion source chamber having a gas inlet and outlet, and a high-energy, pulsed, ultraviolet laser for ablating the single particles in the high velocity gas flow entering the ion source chamber through the gas inlet to produce positively- and negatively-charged ions. The system further includes a first extraction plate for extracting the positively-charged ions provided in the ion source chamber, and a second extraction plate for extracting the negatively-charged ions provided in the ion source chamber. The positively-charged ions are injected into a first ion mobility spectrometer where they are detected and characterized. The negatively-charged ions are injected into a second ion mobility spectrometer where they are detected and characterized. The dual ion mobility spectrometers configuration of the present invention permits characterization of both the positively- and negatively-charged ions from a single gas particle.

11 Claims, 3 Drawing Sheets

SYSTEM AND METHOD FOR CHEMICAL ANALYSIS USING LASER ABLATION

The present application claims the benefit of International Application No. PCT/US01/18468, filed Jun. 7, 2001, which is based on U.S. Provisional Patent Application Serial No. 60/210,610, filed Jun. 9, 2000.

CLAIM FOR PRIORITY AND GOVERNMENT RIGHTS

The present application has Government rights assigned to the Environmental Protection Agency under Contract Number R82-6769-010.

BACKGROUND OF THE INVENTION

A. Field of the Invention

The present invention relates generally to chemical analysis of aerosols, and, more particularly to a system and method for chemical analysis of individual particles in a high velocity gas flow using laser ablation ion mobility spectrometry.

B. Description of the Related Art

Time-of-flight mass spectrometry is a well-known technique for quickly and accurately providing ion mass information. Time-of-flight mass spectrometry systems accelerate ions, via an electric field, toward a field-free flight tube which terminates at an ion detector. In accordance with known time-of-flight mass spectrometry principles, ion flight time is a function of ion mass so that ions having less mass arrive at the detector more quickly than those having greater mass. Ion mass can thus be computed from ion flight time through the instrument.

Another known ion separation technique which may be used to separate the bulk of the ions in time is ion mobility spectrometry. Ion mobility spectrometry instruments typically include a pressurized static buffer gas contained in a drift tube which defines a constant electric field from one end of the tube to the other. Gaseous ions entering the constant electric field area are accelerated thereby and experience repeated collisions with the buffer gas molecules as they travel through the drift tube. As a result of the repeated accelerations and collisions, each of the gaseous ions achieves a constant velocity through the drift tube. The ratio of ion velocity to the magnitude of the electric field defines an ion's mobility, wherein the mobility of any given ion through a high pressure buffer gas is a function of the collision cross-section of the ion with the buffer gas and the charge of the ion.

Time-of-flight mass spectrometry has the ability to simultaneously analyze all ions from each particle. This capability is also shared by other known mass spectrometry methods such as Fourier transform ion cyclotron resonance and quadruple ion trap. The disadvantages of these techniques is the need to operate under high vacuum conditions which adds complexity, size, and cost to the test instrument. Ion mobility spectrometry overcomes these limitations be permitting ion analysis to be performed at a pressure close to atmospheric pressure. Ion mobility spectrometry also retains the ability to simultaneously analyze all ions from each particle. However, there is a need in the art to analyze individual particles in a high velocity gas flow.

SUMMARY OF THE INVENTION

The present invention satisfies this need by providing a system and method for chemical analysis of individual particles in a high velocity gas flow. The present invention further provides an ion mobility spectrometry system and method that analyzes individual particles in a high velocity gas flow.

Additional objects and advantages of the invention will be set forth in part in the description which follows, and in part will be learned from the description, or may be learned by practice of the invention. The objects and advantages of the invention will be realized and attained by means of the and combinations particularly pointed out in the appended claims.

To achieve the objects and in accordance with the purpose of the invention, as embodied and broadly described herein, the invention comprises a system for chemical analysis of single particles in a high velocity gas flow, the system comprising: an ion source chamber; a laser for ablating the single particles in the high velocity gas flow entering the ion source chamber to produce positively- and negatively-charged ions from each single particle; means for extracting the positively-charged ions provided in the ion source chamber; means for extracting the negatively-charged ions provided in the ion source chamber; a first ion mobility spectrometer connected to the positively-charged ion extracting means and characterizing and detecting the positively-charged ions; and a second ion mobility spectrometer connected to the negatively-charged ion extracting means and characterizing and detecting the negatively-charged ions.

To further achieve the objects and in accordance with the purpose of the invention, as embodied and broadly described herein, the invention comprises a method for chemical analysis of single particles in a high velocity gas flow, the method comprising the steps of: introducing the gas into an ion source chamber; ablating the single particles in the high velocity gas flow entering the ion source chamber with a laser to produce positively- and negatively-charged ions from each single particle; extracting the positively-charged ions from the ion source chamber; extracting the negatively-charged ions from the ion source chamber; characterizing and detecting the positively-charged ions with a first ion mobility spectrometer; and characterizing and detecting the negatively-charged ions with a second ion mobility spectrometer.

It is to be understood that both the foregoing general description and the following detailed description are exemplary and explanatory only and are not restrictive of the invention, as claimed.

DESCRIPTION OF THE DRAWINGS

The accompanying drawings, which are incorporated in and constitute a part of this specification, illustrate one embodiment of the invention and together with the description, serve to explain the principles of the invention. In the drawings.

DESCRIPTION OF THE PREFERRED EMBODIMENT

Reference will now be made in detail to the present preferred embodiment of the invention, an example of which is illustrated in the accompanying drawings. Wherever possible, the same reference numbers will be used throughout the drawings to refer to the same or like parts.

In accordance with the invention, the present invention is broadly drawn to a system and method for real-time chemical analysis of single particles in a high velocity gas flow using laser ablation and dual ion mobility spectrometers. As used herein, the term "high velocity gas flow" means a gas flow traveling at a velocity up to 400 meters/second (m/s), with particles traveling at a velocity of up to 150 m/s.

Figure 1:
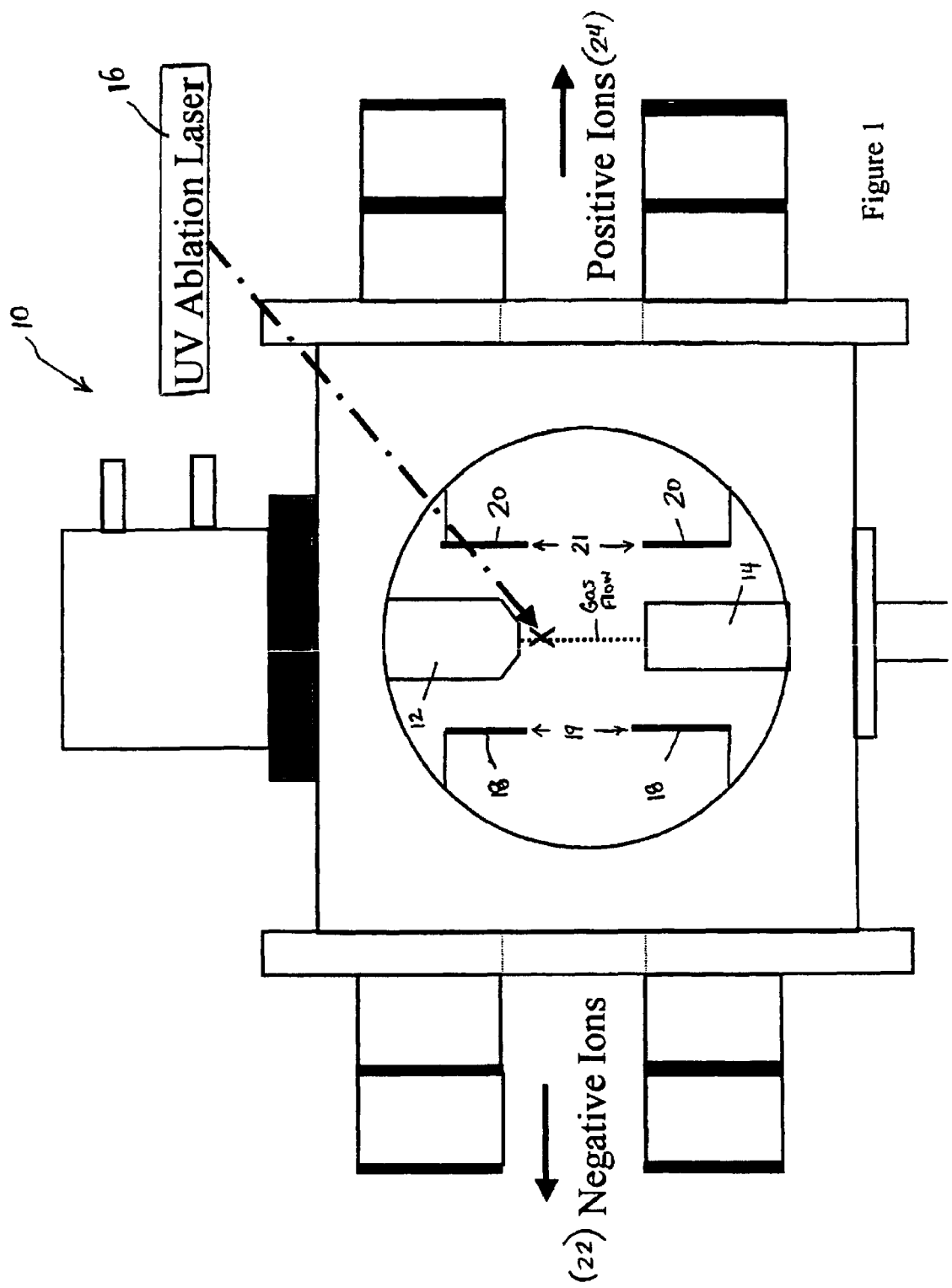
FIG. 1 is a schematic diagram of an ion source chamber used in the system of the present invention.
Figure 2:
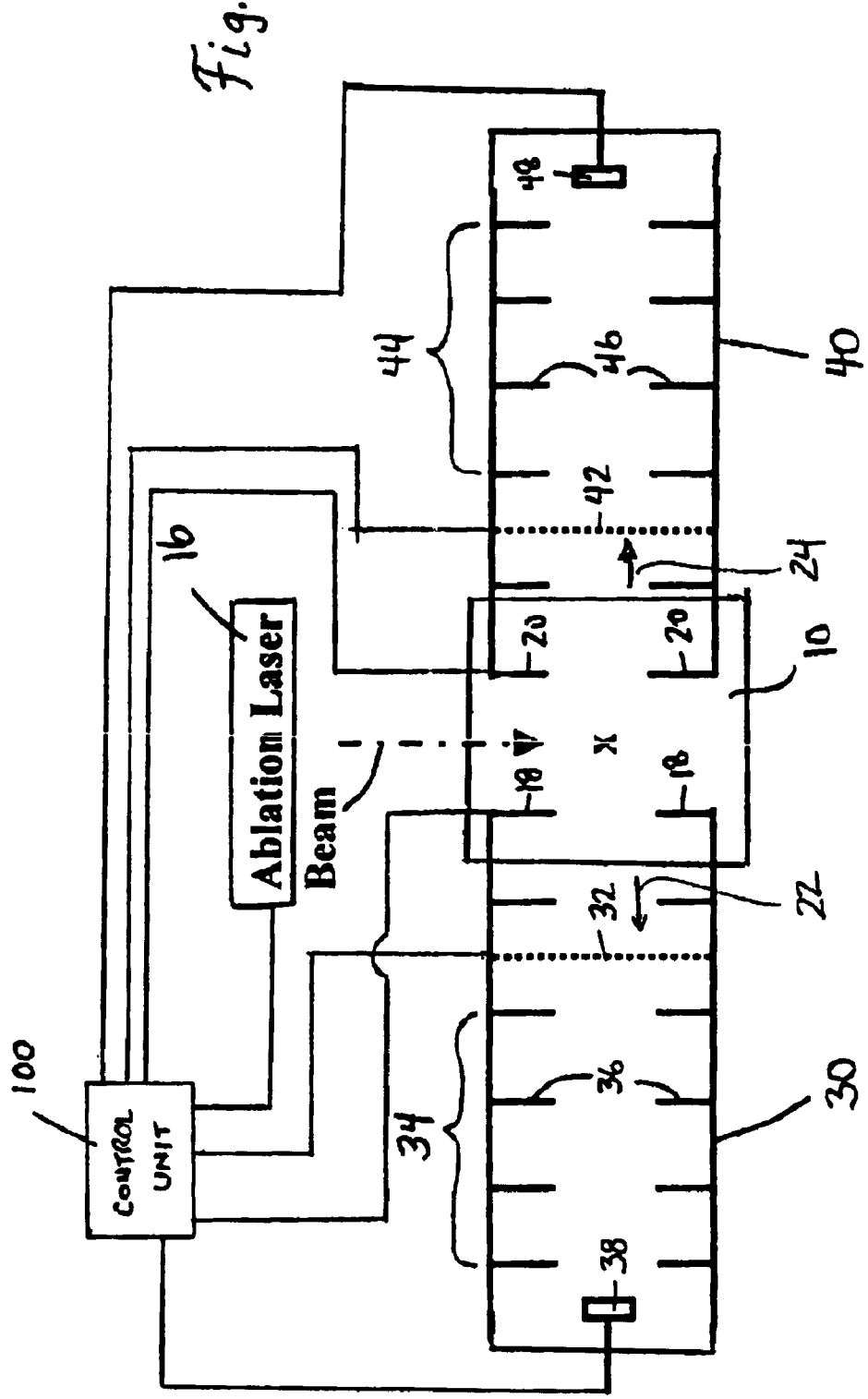
FIG. 2 is a schematic diagram of the overall system of the present invention, including the dual ion mobility spectrometers of the present invention.
Figure 3:
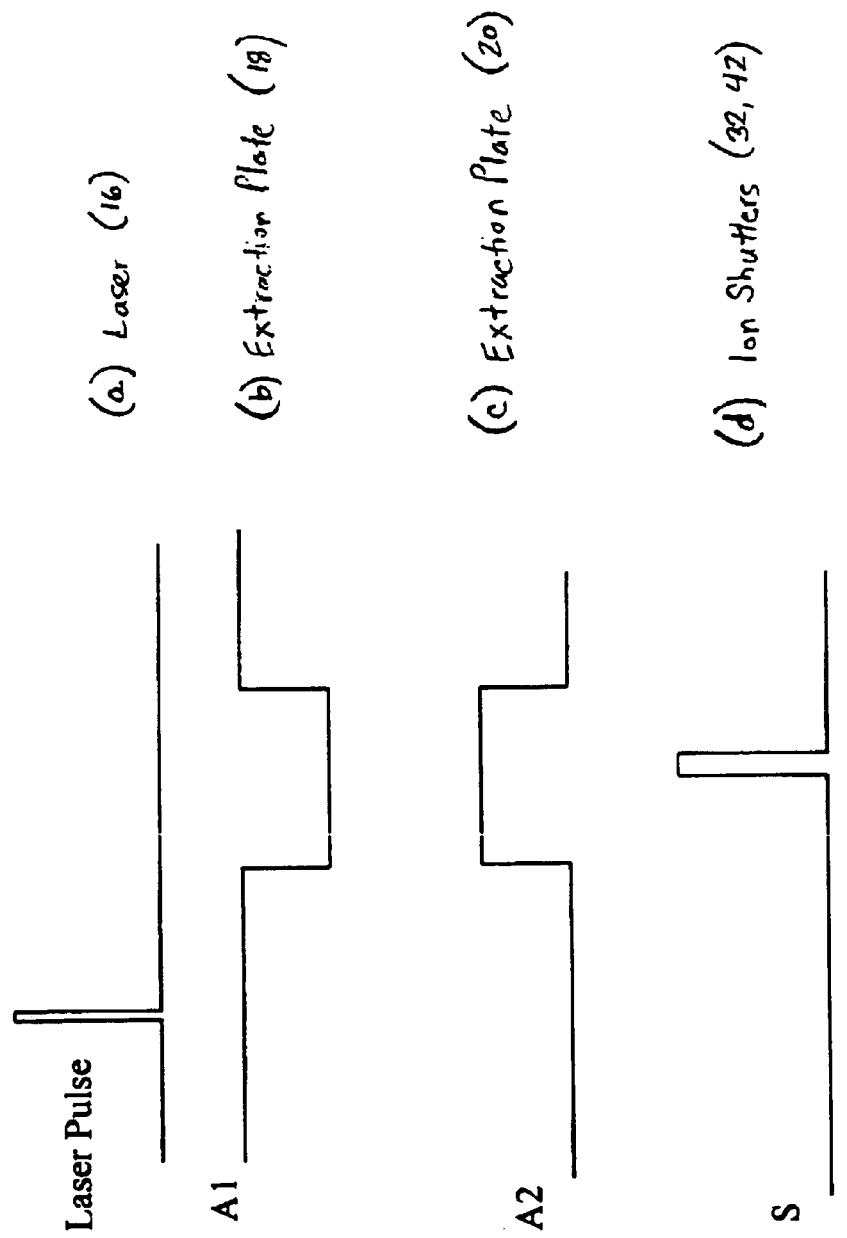
FIGS. 3(a)–3(d) show timing diagrams for a laser pulse, extraction plates, and an ion shutter used in the system of the present invention.

The overall system of the present invention is shown in FIG. 2, and includes the ion source chamber 10 shown in FIG. 1. As embodied herein and as shown in FIG. 1, a gas enters ion source chamber 10 at a high velocity through a gas inlet 12. Individual particles in the gas entering ion source chamber 10 are ablated with a laser 16 to produce positively- and negatively-charged ions from each gas particle. Preferably, laser 16 is a high-energy, pulsed, ultraviolet laser. Any gas remaining after the laser ablation exits ion source chamber 10 through a gas outlet 14. A pair of ion extraction plates 18, 20 lie adjacent, and, preferably, orthogonal to the gas flow to extract ions therefrom. Voltage pulses, preferably high voltage pulses, are applied to extraction plates 18, 20 to establish a high electric field gradient therebetween. The voltage pulses applied to extraction plates 18, 20 may vary, however, applying a potential difference of 5000 volts (i.e., applying a +2500 volt pulse to one plate, and applying a −2500 volt pulse to the other plate) between plates 18, 20 works quite well. The electric field gradient extracts ions from the gas flow through apertures 19, 21 in the plates 18, 20. Positively- and negatively-charged ions are extracted in opposite directions, with negatively-charged ions 22 being extracted by plate 18 and positively-charged ions 24 being extracted by plate 20. Alternatively, extraction plate 18 could extract positively-charged ions 24, and extraction plate 20 could extract negatively-charged ions 22. The type of ions extracted by extraction plates 18, 20 depends upon the polarity of the voltage pulses applies to plates 18, 20 (e.g., ±2500 volts), wherein a negative voltage pulse applied to an extraction plate will attract positively-charged ions, and a positive voltage pulse applied to an extraction plate will attract negatively-charged ions.

As shown in FIG. 2, the negatively-charged ions 22 are injected into an ion mobility spectrometer 30. Ion mobility spectrometer 30 includes an ion shutter 32 that receives a voltage pulse at a certain time to maximize the resolution of the mobility analysis, a drift tube 34 having a plurality of plates 36 with apertures provided therein, and a Faraday cup 38. Although a plurality of plates are shown in FIG. 2, drift tube 34 may also have only a single plate 36. After passing through aperture 19 (shown in FIG. 1) of extraction plate 18, the negatively-charged ions 22 become trapped in ion shutter 32. Subsequently, the voltage applied to ion shutter 32 is pulsed to a new value to allow the trapped negatively-charged ions 22 to enter into drift tube 34 and eventually strike Faraday cup 38. This allows the negatively-charged ions 22 to be characterized and detected.

Similarly, the positively-charged ions 24 are injected into another ion mobility spectrometer 40. Like spectrometer 30, ion mobility spectrometer 40 includes an ion shutter 42 that receives a voltage pulse at a certain time to maximize the resolution of the mobility analysis, a drift tube 44 having a plurality of plates 46 with apertures provided therein, and a Faraday cup 48. Upon entering aperture 21 (shown in FIG. 1) of extraction plate 20, the positively-charged ions 24 become trapped. Subsequently, the voltage applied to extraction plate 20 is pulsed to a new value to allow the trapped positively-charged ions 24 to enter into ion shutter 42 and drift tube 44 and eventually strike Faraday cup 48. This allows the positively-charged ions 24 to be characterized and detected.

Although there is no preferred voltage applied to ion shutters 32, 42, the voltage applied to these shutters 32, 42 needs to be large enough so that shutters 32, 42 may act like shutters, that is, either allow ions to pass through, or prevent ions from passing through.

As shown in FIG. 2, laser 16, extraction plates 18, 20, ion shutters 32, 42, and Faraday cups 38, 48 are all interconnected to a control unit 100, which may be any conventional controller, such as a programmable logic controller (PLC), a general purpose personal computer programmed with control software, etc. Control unit 100 determines when laser 16, extraction plates 18, 20, and ion shutters 32, 42 are to be pulsed, records the arrival time of the ions at Faraday cups 38, 48, and, according to conventional ion mobility techniques, as described in Gary A. Eiceman and Zeev Carpas, *Ion Mobility Spectrometry* (CRC Press, Boca Raton, Fla. 1994), characterizes the ions by the elapsed or drift time thereof. Thus, the size and chemical composition of individual particles in a high velocity gas flow may be determined. FIGS. 3(a)–3(d) show the timing diagrams for when laser 16 is pulsed, when extraction plates 18, 20 are pulsed, and when ion shutters 32, 42 are pulsed, respectively.

The dual ion mobility spectrometer configuration of the present invention allows characterization of both the positively- and negatively-charged ions from a single particle in a high velocity gas flow. The present invention may be used to provide the size and chemical composition of ambient air particles, making the invention useful in pollution monitoring, industrial hygiene, and atmospheric chemistry studies.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for chemical analysis of single particles a high velocity gas flow, the system comprising:
   an ion source chamber;
   a laser for ablating the single particles in the high velocity gas flow entering the ion source chamber to produce positively-charged ions and negatively-charged ions from each single particle;
   means for extracting the positively-charged ions provided in the ion source chamber;
   means for extracting the negatively-charged ions provided in the ion source chamber;
   a first ion mobility spectrometer connected to the positively-charged ion extracting means and characterizing and detecting the positively-charged ions; and
   a second ion mobility spectrometer connected to the negatively-charged ion extracting means and characterizing and detecting the negatively-charged ions.

2. A system as recited in claim 1, wherein the means for extracting the positively-charged ions comprises an ion extraction plate arranged adjacent and orthogonal to the high velocity gas flow.

3. A system as recited in claim 1, wherein the means for extracting the negatively-charged ions comprises anion extraction plate arranged adjacent and orthogonal to the high velocity gas flow.

4. A system as recited in claim 1, further comprising:
a control unit connected to the laser, the means for extracting the positively-charged ions, the means for extracting the negatively-charged ions, and the first and second ion mobility spectrometers, the control unit determining the size and chemical composition of the single particles based upon the positively-charged and negatively-charged ions characterized and detected in the first and second ion mobility spectrometers.

5. A system as recited in claim 1, wherein the laser comprises a high-energy, pulsed, ultraviolet laser.

6. A system for chemical analysis of single particles in a high velocity gas flow, the system comprising:
an ion source chamber;
a laser for ablating the single particles in the high velocity gas flow entering the ion source chamber to produce positively-charged ions and negatively-charged ions from each single particle;
a first ion extraction plate arranged adjacent and orthogonal to the high velocity gas flow for extracting the positively-charged ions;
a second ion extraction plate arranged adjacent and orthogonal to the high velocity gas flow for extracting the negatively-charged ions;
a first ion mobility spectrometer connected to the positively-charged ion extracting means and characterizing and detecting the positively-charged ions;
a second ion mobility spectrometer connected to the negatively-charged ion extracting means and characterizing and detecting the negatively-charged ions; and
a control unit connected to the laser, the first and second ion extraction plates, and the first and second ion mobility spectrometers, the control unit determining the size and chemical composition of the single particles based upon the positively-charged and negatively-charged ions characterized and detected in the first and second ion mobility spectrometers.

7. A system as recited in claim 6, wherein the laser comprises a high-energy, pulsed, ultraviolet laser.

8. A method for chemical analysis of single particles in a high velocity gas flow, the method comprising the steps of:
introducing the gas into an ion source chamber;
ablating the single particles in the high velocity gas flow entering the ion source chamber with a laser to produce positively-charged ions and negatively-charged ions from each single particle;
extracting the positively-charged ions from the ion source chamber;
extracting the negatively-charged ions from the ion source chamber;
characterizing and detecting the positively-charged ions with a first ion mobility spectrometer; and
characterizing and detecting the negatively-charged ions with a second ion mobility spectrometer.

9. A method as recited in claim 8, wherein the positively-charged ions are extracted by an ion extraction plate.

10. A method as recited in claim 9, wherein the negatively-charged ions are extracted by another ion extraction plate.

11. A method as recited in claim 10, further comprising:
connecting a control unit to the laser, the ion extraction plates, and the first and second ion mobility spectrometers; and
determining, with the control unit, the size and chemical composition of the single particles based upon the positively-charged and negatively-charged ions characterized and detected in the first and second ion mobility spectrometers.

* * * * *

UNITED STATES PATENT AND TRADEMARK OFFICE
CERTIFICATE OF CORRECTION

PATENT NO. : 6,815,671 B2
DATED : December 22, 2004
INVENTOR(S) : Murray V. Johnston, Jr. et al.

It is certified that error appears in the above-identified patent and that said Letters Patent is hereby corrected as shown below:

Column 4,
Line 42, after "particles" insert -- in --.
Line 65, after "comprises" delete "anion" and insert -- an ion --.

Signed and Sealed this

First Day of March, 2005

JON W. DUDAS
*Director of the United States Patent and Trademark Office*